US009008269B2

(12) United States Patent
Wang et al.

(10) Patent No.: US 9,008,269 B2
(45) Date of Patent: Apr. 14, 2015

(54) METHOD AND APPARATUS FOR ADJUSTING A FIELD OF VIEW FOR EXPOSURE OF AN X-RAY SYSTEM, AND AN X-RAY SYSTEM

(75) Inventors: Jian Wang, Beijing (CN); Bin Ye, Beijing (CN); Yannan Huang, Beijing (CN); Yonghui Han, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 232 days.

(21) Appl. No.: 13/598,643

(22) Filed: Aug. 30, 2012

(65) Prior Publication Data

US 2013/0077745 A1 Mar. 28, 2013

(30) Foreign Application Priority Data

Aug. 31, 2011 (CN) .......................... 2011 1 0289147

(51) Int. Cl.
*A61B 6/08* (2006.01)
*A61B 6/00* (2006.01)
*A61B 6/06* (2006.01)

(52) U.S. Cl.
CPC ... *A61B 6/52* (2013.01); *A61B 6/06* (2013.01); *A61B 6/08* (2013.01); *A61B 6/469* (2013.01); *A61B 6/4021* (2013.01); *A61B 6/548* (2013.01)

(58) Field of Classification Search
CPC .......... A61B 6/00; A61B 6/08; A61B 6/5241; A61B 6/027; A61B 6/032; A61B 6/497; A61B 6/469; A61B 6/544; A61B 6/06
See application file for complete search history.

(56) References Cited

U.S. PATENT DOCUMENTS

| 4,323,779 A | * | 4/1982 | Albert | 378/98.6 |
| 5,485,500 A | * | 1/1996 | Baba et al. | 378/98.2 |
| 6,445,761 B1 | * | 9/2002 | Miyazaki et al. | 378/8 |
| 6,895,076 B2 | * | 5/2005 | Halsmer et al. | 378/98.12 |
| 7,110,497 B2 | * | 9/2006 | Halsmer et al. | 378/98.12 |
| 7,170,967 B2 | * | 1/2007 | Cherek et al. | 378/20 |
| 7,742,570 B2 | * | 6/2010 | Yamaguchi | 378/98.12 |
| 7,764,762 B2 | * | 7/2010 | Sendai | 378/8 |

(Continued)

FOREIGN PATENT DOCUMENTS

DE 102009051897 A1 5/2011

OTHER PUBLICATIONS

Search Report and Written Opinion from corresponding EP Application No. 12181963.5 dated Feb. 5, 2013.

*Primary Examiner* — David A Vanore
(74) *Attorney, Agent, or Firm* — GE Global Patent Operation; Marc A. Vivenzio

(57) ABSTRACT

A method for adjusting a field of view for exposure of an X-ray system is provided. The method comprises: capturing an image of a patient on an examining table of the system by an image sensor, wherein the image sensor is placed at a predetermined position in the system; displaying the captured image on a display for selection of a region of interest or a point of interest by a user on the image; automatically determining a target position of an X-ray source in response to the selection of the region of interest or the point of interest on the image, wherein a desired field of view for exposure covering the region of interest or the point of interest is obtained when the X-ray source is located at the target position; and automatically locating the X-ray source at the target position in response to the determination of the target position.

20 Claims, 5 Drawing Sheets

(56) References Cited

U.S. PATENT DOCUMENTS

| | | | |
|---|---|---|---|
| 2001/0016029 A1* | 8/2001 | Tumer | 378/98.8 |
| 2002/0118280 A1 | 8/2002 | Medlar et al. | |
| 2004/0082852 A1* | 4/2004 | Cherek et al. | 600/427 |
| 2005/0169427 A1* | 8/2005 | Halsmer et al. | 378/98.12 |
| 2008/0056435 A1* | 3/2008 | Basu et al. | 378/9 |
| 2009/0232271 A1 | 9/2009 | Sendai | |
| 2011/0164728 A1* | 7/2011 | Tsuchiya et al. | 378/62 |
| 2012/0275563 A1* | 11/2012 | Manak et al. | 378/62 |
| 2013/0308746 A1* | 11/2013 | Ueki | 378/9 |
| 2014/0105356 A1* | 4/2014 | Yin et al. | 378/62 |
| 2014/0185751 A1* | 7/2014 | De Man et al. | 378/51 |

* cited by examiner

METHOD AND APPARATUS FOR ADJUSTING A FIELD OF VIEW FOR EXPOSURE OF AN X-RAY SYSTEM, AND AN X-RAY SYSTEM

BACKGROUND OF THE INVENTION

Embodiments of the invention relate to X-ray systems, and in particular to a method and apparatus for adjusting a field of view for exposure of an x-ray system, and an X-ray system.

FIG. 1 shows a prior art digital X-ray system 100 that includes an Overhead Tube Suspensory (OTS) system 101 for moving an X-ray source, an OTS console 102, a collimator 103 constituting the X-ray source (other components constituting the X-ray source are not shown due to the angle of view), a movable examining table 104, and a positioner 105 for moving the examining table 104. The collimator 103 is typically mounted below the tube that emits X-rays, which impinges upon the patient through a shutter of the collimator 103, wherein the size of the shutter of the collimator 103 defines the irradiation range of X-rays, i.e., the size of the region of the field of view for exposure (FOV) 106. The lateral positions of the tube and the collimator determine the position of the field of view for exposure on the patient. It is well known that X-rays are harmful to humans, thus it is required that X-rays are controlled so that it impinges only upon the part to be examined, of the patient, while its irradiation range should be large enough to satisfy all of regions to be examined.

In the current digital X-ray system 100, for each X-ray examination, a radiographer is required to check whether the field of view for exposure 106 of X-ray is suitable or not. During checking, the radiographer turns on the illumination light of the collimator 103, and a collimator beam 107 will form an exposure region on the patient. The exposure region is consistent with the field of view for exposure 106 of the X-ray, so that whether the field of view for exposure 106 is suitable or not may be checked. If the field of view for exposure can not satisfy exposure requirement, the size and position of the field of view are required to be adjusted. The position of the X-ray source may be adjusted by manually moving the OTS and/or the positioner, to adjust the position of the FOV on the patient. For an advanced X-ray system, it is often equipped with an automatic positioning function, which can help the radiographer in controlling the OTS so as to automatically move into the preset position. However, existing digital X-ray systems only can preset a limited number of positions for automatic positioning, and the preset position should be selected by a radiographer before automatically positioning at the preset position.

For a hospital with heavy load, a radiographer may often deal with various patients. The limited number of preset positions in the existing digital X-ray systems is far from satisfying clinical needs. In addition, during the practical operation, a radiographer often needs to manually adjust the positioner of the X-ray system, in order to better adjust the position of the field of view for exposure. Generally, in some hospitals, it may need to image several hundreds of patients every day, and during the diagnosis, the field of view for exposure of the X-ray system should be manually adjusted almost for each patient, which, for a radiographer, particularly for a female radiographer, is a huge challenge.

In addition, when a radiographer wants to ensure that the region of the field of view is acceptable, he needs to turn on the lamp of the collimator, and at this time, a laser cross cursor for demarcating the position of the detector appears; however, the laser cross cursor is not patient friendly, and sometimes may hurt eyes of the patient.

Currently, each protocol in an X-ray system is provided with a default FOV value (i.e., the size of the FOV region). However, the default value may sometimes not be suitable for a patient whose body size is rather different. At this time, a radiographer is required to manually modify the FOV value, which will increase the time required for the whole examination and the work flow. If the radiographer is unwilling to manually modify the FOV value, some patients may expose to excessive dose of radiation which will be very dangerous.

BRIEF DESCRIPTION OF THE INVENTION

According to an embodiment of the present invention, a method for automatically adjusting the field of view for exposure of an X-ray system is provided. The method comprises: capturing an image of a patient on an examining table of the X-ray system by an image sensor, wherein the image sensor is placed at a predetermined position in the X-ray system; displaying the captured image on a display for selection of a region of interest or a point of interest by a user on the image; automatically determining a target position of an X-ray source in response to the selection of the region of interest or the point of interest on the image, wherein a desired field of view for exposure covering the region of interest or the point of interest is obtained when the X-ray source is located at the target position; and automatically locating the X-ray source at the target position in response to the determination of the target position.

According to another embodiment of the invention, an X-ray system is provided. The X-ray system comprises: an X-ray source for emitting an X-ray to form a field of view for exposure on a patient; an image sensor arranged at a predetermined position in the X-ray system for capturing an image of the patient; a display for displaying the captured image of the patient for selection of a region of interest or a point of interest by a user on the image; a computing device configured to compute a target position of the X-ray source, wherein a desired field of view for exposure covering the region of interest or the point of interest is obtained when the X-ray source is located at the target position; a shifting device for locating the X-ray source at the target position; and a control device configured to control the computing device to start computing the target position in response to the selection of the region of interest or the point of interest, and to control the shifting device to locate the X-ray source at the target position in response to the computed target position.

According to another embodiment of the present invention, an automatic adjusting device of a field of view for exposure for an X-ray system is provided. The automatic adjusting device comprises: an image sensor arranged at a predetermined position in the X-ray system, for capturing an image of a patient to be examined on an examining table, and for transmitting the captured image to a display for selection of a region of interest or a point of interest by a user; a computing device configured to compute a target position of an X-ray source in the X-ray system, wherein a desired field of view for exposure covering the region of interest or the point of interest selected by the user is obtained when the X-ray source is located at the target position; and a control device configured to control the computing device to start computing the target position in response to the selection of the region of interest or the point of interest by the user on the captured image, and to send a locating signal to the X-ray system to locate the X-ray source at the target position in response to the computed target position.

BRIEF DESCRIPTION OF THE DRAWINGS

The content of this disclosure will be understood more thoroughly from reading the following detailed description in conjunction with accompanying drawings, wherein.

DETAILED DESCRIPTION OF THE INVENTION

Figure 2:
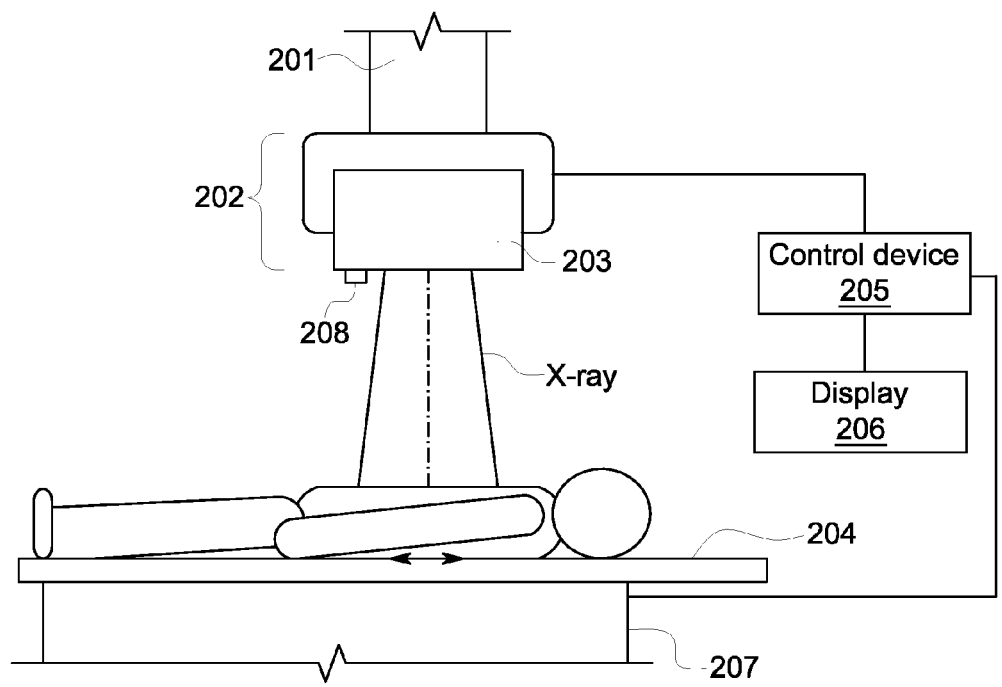
FIG. 2 is a schematic diagram of an X-ray system that may automatically adjust the field of view for exposure as needed, according to an embodiment of the present invention.

FIG. 2 is a schematic diagram of an X-ray system 200 according to an embodiment of the present invention. As shown in the figure, the X-ray system 200 includes an overhead tube suspensory system 201, an X-ray source 202, an examining table 204, a positioner 207 for moving the examining table, a control device 204 and a display 205. In addition, the X-ray system 200 includes an image sensor 208, which is fixed at a predetermined position in the X-ray system, for imaging the patient on the examining table 204. The image sensor 208 may be any of now known or later developed apparatus that can take an image, hereinafter an embodiment of the present invention will be explained by taking a digital camera as an example of the image sensor 208. The camera 208 is fixed at a position where it can capture an image of the patient on the examining table 204, and a distance of the position from other devices in the X-ray system 200 is measurable or known. In the embodiment shown in FIG. 2, the camera 208 is fixed on the lower surface (i.e., the surface on which the collimator shutter is located) of the collimator 203 that is a part of the X-ray source, and is nearly flush with the surface. In one embodiment, the distance of the camera 208 from the center of the collimator shutter is about several centimeters. For simplicity, in the following embodiments, the position of the center of the collimator shutter in the X-ray source is regarded as the position of the X-ray source, therefore, the projection of the position of the X-ray source upon the patient is just the position of the center of the field of view for exposure. Of course, position of other point or points on the X-ray source may be regarded as the position of the X-ray source, and with the determination of the position of the center of the collimator shutter, it is easy to obtain the position of the other point or points.

Figure 1:
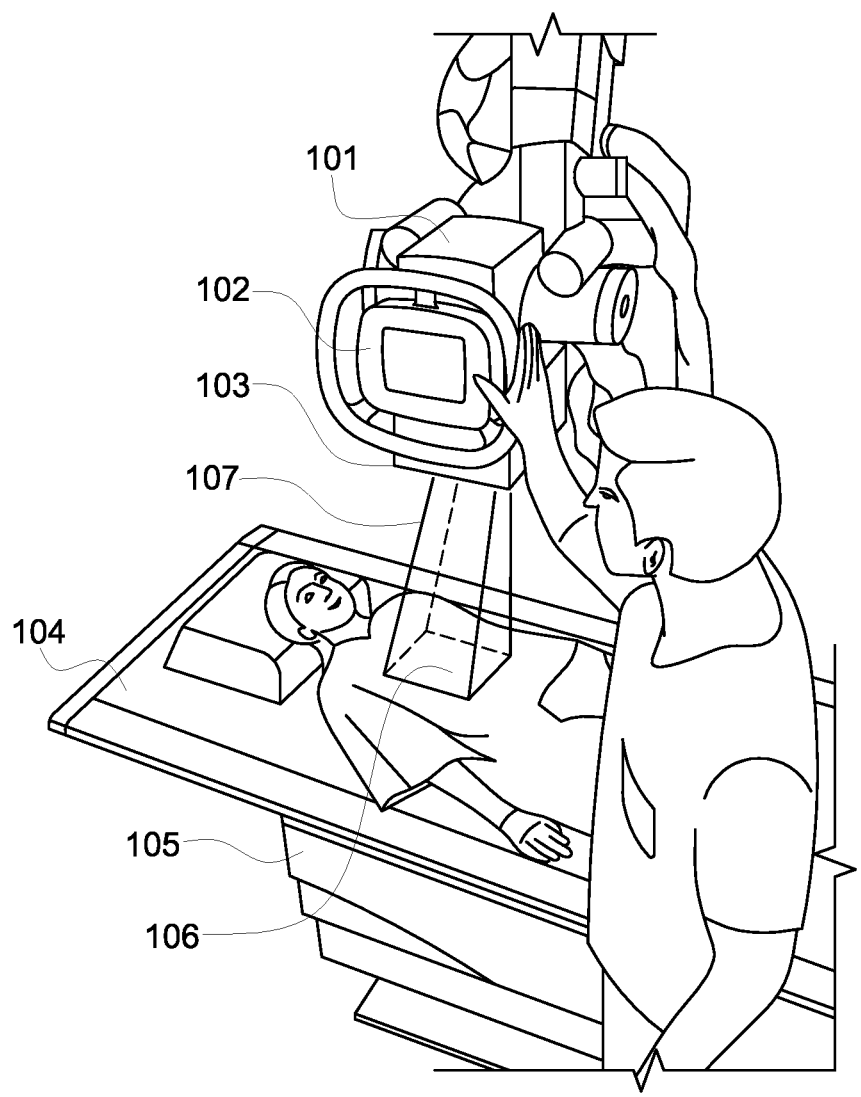
FIG. 1 is a schematic diagram of a prior art X-ray system, in which the field of view for exposure of the X-ray system needs to be adjusted manually.

The X-ray system 200 also includes a control device 205 and a display 206. Although the control device 205 and the display 206 are shown in FIG. 2 as being separated from the overhead tube suspensory system (OTS) 201 and the X-ray source 202 by a distance and communicating via cables, it will be appreciated by one skilled in the art that the control device 205 and the display 206 may be the control device and the display of the OTS console as shown in FIG. 1, or may be the control and the display of the remote workstation in wired or wireless communication with the OTS console, or may also be the control device and the display of the portable console in wireless communication with the OTS console or the workstation, or any combination thereof.

Figure 4:
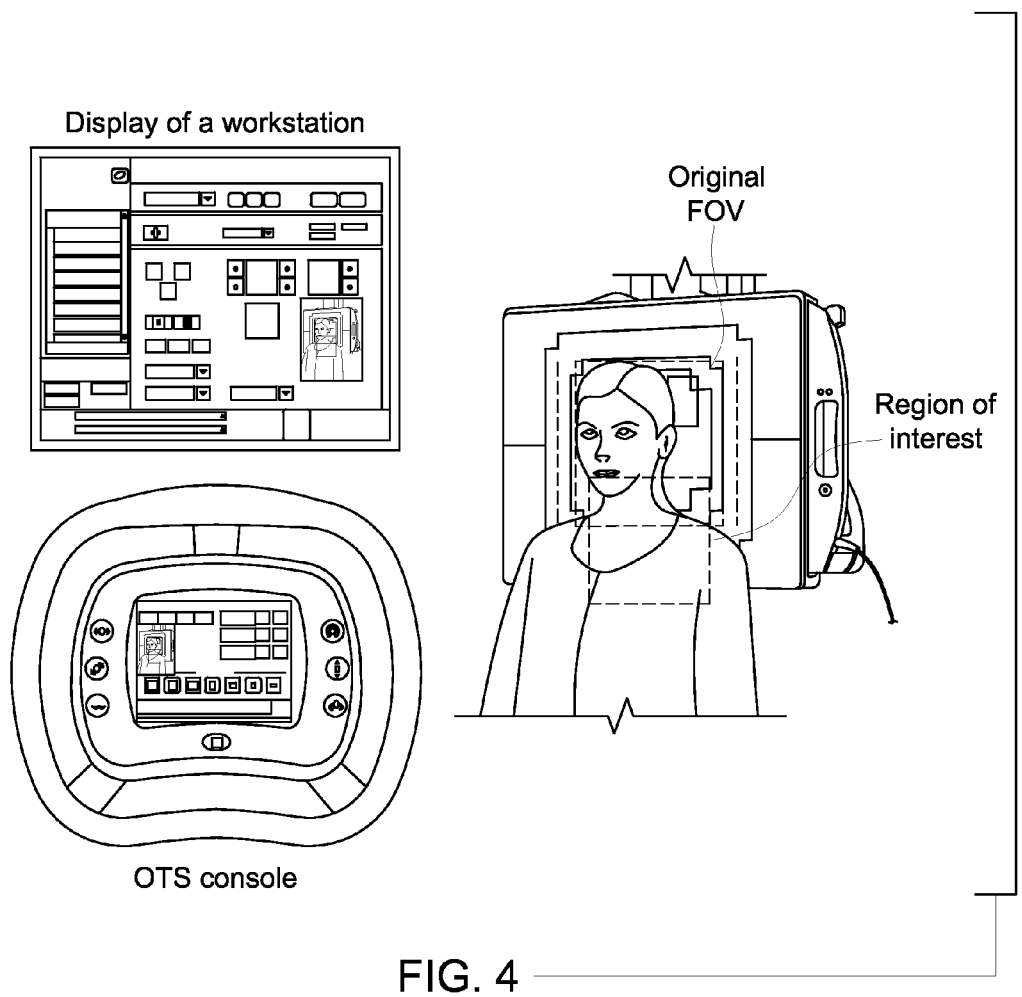
FIG. 4 is a schematic diagram of an image of a patient captured by an X-ray system according to embodiments of the present invention.

The image of the patient captured by the camera 208 is transmitted to the control device 205 and displayed on the display 206. FIG. 4 is a schematic diagram illustrating the image of the patient captured by the X-ray system according to embodiments of the present invention, in which FIG. 4A is a schematic diagram of the image on the display of the OTS console, FIG. 4B is a schematic diagram of the image on the display of the workstation, and FIG. 4C is an enlarged view of the captured image of the patient.

An operator of the X-ray system 200 uses a pointing device, such as a mouse to select the desirable region of interest or point of interest on the image of the patient that is displayed on the display. In addition, in the case where the display is a touch screen, the operator may directly touch the touch screen with his/her finger or a device such as a pen to select the region of interest or the point of interest.

Returning to FIG. 2, the X-ray system 200 also includes a computing device 209 for computing the target position of the X-ray source corresponding to the selected region of interest or point of interest. When the X-ray source is at the target position, the X-ray emitted therefrom forms the desired field of view for exposure on the patient, that is, the region of interest or the point of interest falls within the desired field of view for exposure. After the control device 205 detects the selection of the region of interest or the point of interest, it sends to the computing device 209 a control signal to start computation. After the computing device 209 receives the signal, it starts computing the target position of the X-ray source, and returns the computed target position to the control device 205. The control device 205 subsequently controls the OTS 201 to move the X-ray source to the target position. The target position of the X-ray source is actually a relative position relative to the patient. In another embodiment, the control device 205 may also move the patient by controlling the positioner 207 for moving the examining table 204, so as to locate the X-ray source at the target position, thereby obtaining the desired field of view for exposure. In other embodiments, the control device 205 may also locate the X-ray source at the target position by simultaneously controlling both the OTS 201 and the positioner 207 to move both the X-ray source and the patient.

The computing method of the target position of the X-ray source will be described in more detail below. To compute the target position of the X-ray source, it is necessary to utilize the mutual relation between three-dimensional coordinates of a point in space and its corresponding two-dimensional coordinates of the image. To determine the mutual relation between three-dimensional coordinates of a point in space and its corresponding two-dimensional coordinates of the image, it is required to build the geometrical model of the image sensor (taking the camera as an example) imaging, and determine the geometrical model parameters thereof (herein referred to as imaging parameters), this process is referred to as camera demarcating.

The basic idea of a camera demarcating algorithm is to select a known object in space as a demarcating reference, on which the image processing and a series of mathematical transforming and computing methods are performed, so as to compute internal parameters and external parameters of the camera. The internal parameters include parameters such as a camera lens focus, a lens distortion coefficient, an image coordinate origin, and the external parameters include horizontal and rotating shift of the object relative to the camera lens.

The accuracy of the camera demarcating has great influence on subsequent processing, and is one of very critical steps. To select a demarcating algorithm satisfying requirements, the inventor investigates a variety of demarcating algorithms outlined as follows:

1. Demarcating Method Utilizing a Optimization Algorithm:

The method proposed by FAIG is a typical example of this kind of technology; this method utilizes coplanar constraint condition of a pinhole camera model. It is assumed that the optical imaging model of a camera is very complicated, considering various factors during imaging of the camera, each image requires 17 parameters to complete the demarcating function, and is computation intensive.

An advantage of this algorithm is being capable of assuming the optical imaging model of a camera is very complicated. However, its disadvantage is that the result of demarcating depends on the initially given value, and if the initially given value is not proper, it is difficult to get the correct result through optimization; in addition, the optimization program is time-consuming, and the result cannot be given in real time.

2. Direct Linear Transforming Method:

Karara proposed that directly solving a linear transformation may complete the solution of the model parameters in camera demarcating, which is attractive. A disadvantage of the method is that the influence of non-linear distortion factors of the lens is not considered, thus there is a relatively larger error. When there is high requirement on the accuracy, the linear model often cannot exactly describe the correspondence relation between geometrical model computations, therefore a non-linear model should be used.

3. Two-Step Method:

Tsai proposed a two-step method based on radial constraint condition. The method first utilizes the radial constrain condition to solve the external parameters of the camera, and then solve other parameters of the camera. The method has a high accuracy, but a disadvantage is high requirements on equipment. Therefore, the accuracy of the method is at the cost of the complexity of the algorithm and equipment.

4. Zhengyou Zhang's Demarcating Method:

This method assumes that the demarcating plate plane is in the world coordinate system, z=0, the optimal solution of the parameters is computed by a linear model, and then non-linear refinement is performed based on the maximum likelihood method. This method first demarcates and solves the distortion parameters, and then solves internal and external parameters of the camera. The method is very robust, requires no expensive precise demarcating block, and is practical. However, the model assumes that a straight line remain the same after imaging by the camera, there is large error for a wide-angle camera. For Zhengyou Zhang's demarcating method, see Zhengyou Zhang's "Flexible Camera Calibration By Viewing a Plane From Unknown Orientations", 0-7695-0164-8/99 $10.00 (c) 1999 IEEE.

With the use of various demarcating methods described above, the mutual relation between three-dimensional coordinates of a point in space and its corresponding two-dimensional coordinates of the image, and then the imaging geometrical model and imaging parameters of the camera may be solved. The imaging geometrical model and the imaging parameters may be applied whenever the correspondence between the points of the image captured by the camera and the points in real world is applied later, as long as the lens of the camera is not replaced and the position of the camera in the X-ray system and the shooting angle of view of the camera remain unchanged. In case that the imaging geometrical model and the imaging parameters of the camera are demarcated, knowing the coordinates of a point on the image captured by the camera, its coordinates in real world may be solved, and vice versa.

In response to selection of the region of interest or the point of interest in the image displayed on the display, the computing device 209 first computes the position of the center of the desired field of view for exposure on the image. In one embodiment, the position of the center of the selected region of interest on the image is calculated as the position of the center of the desired field of view for exposure on the image, or the position of the selected point of interest on the image is calculated as the position of the center of the desired field of view for exposure on the image. Then, the computing device 209 utilizes the stored imaging parameters and the imaging geometrical model to calculate the position of the center of the field of view for exposure in real world (i.e., the actual position on the patient), i.e. the projection position of the position of the X-ray source on the patient. In at least one embodiment of the present invention, the height of the X-ray source from the patient remains the same during adjustment. Therefore, knowing the projection position of the X-ray source, it is easy to obtain the real position of the X-ray source, i.e., the target position of the X-ray source.

In one embodiment, the computing device 209 also calculates the actual size of the desired field of view for exposure based on the selected region of interest. First, the computing device 209 computes the coordinates of positions of points which constitute a boundary of the region of interest, on the image, and then determines the coordinates of actual positions of these points on the patient based on the coordinates of the positions of the points on the image and the imaging geometrical model and the imaging parameters of the image sensor. Then, the computing device 209 determines the actual size of the region of interest based on the coordinates of the actual positions of the boundary points, and determines the size of the desired field of view for exposure based on the actual size of the region of interest. Typically, the size of the desired field of view for exposure is selected such that the desired field of view for exposure is entirely overlapped with, or slightly larger than, the region of interest. For a given X-ray system, the relationship between the size of the region of the field of view for exposure and the size of the collimator shutter is known and fixed. According to the relationship and based on the size of the region of the desired field of view for exposure, the computing device 209 may compute the size to which the collimator shutter is adjusted. Therefore, the control device 205 adjusts the collimator, based on the computed size of the collimator shutter, such that the region of the desired field of view for exposure is substantially consistent with, or properly larger than, the region of interest. The known correspondence relation between the size of the collimator shutter and the size of the region of the field of view for exposure is obtained in advance via experiments, and stored in the X-ray system.

Generally, the computing device 209 does not have to compute the coordinates of the positions of all boundary points, and instead, only need to compute the coordinates of the positions of some of the boundary points. For example, the field of view for exposure and the selected region of interest are typically rectangle or square. In this case, the computing device 209 may only compute the coordinates of the positions of the four vertexes of the region of interest on the image, then respectively compute the corresponding coordinates of each vertex in real world, and then may compute the real size of the region of interest and determine the size of the region of the desired field of view for exposure based on the real size. Although rectangle or square region of interest and region of the field of view for exposure are taken as examples hereinabove, it will be appreciated by those skilled in the art that other shapes of the region of interest and the region of the field of view for exposure may be feasible, and the computing method thereof is similar to those described above, and will not be repeated here.

According to an embodiment of the present invention, before an operator selects a region of interest or a point of interest, the position and the region range of a current field of view for exposure are also displayed on the patient image in the display. Therefore, the computing device 209 computes the coordinates of the positions of the center and each vertex of the current field of view for exposure based on the current position of the X-ray source and the size of the collimator shutter, and computes the positions of the center and each vertex on the image based on the imaging geometrical model and the imaging parameters of the camera. Thus, the control device 205 may control the display to display the center and the region range of the current field of view for exposure on the patient image, based on the computed positions of the center and each vertex of the current field of view for exposure on the image. In this way, the operator may visually observe whether the current field of view satisfies requirements without turning on the illumination light of the collimator. If the requirements are satisfied, no adjustment is needed. If the requirements are not satisfied, the adjustment is made by selecting the region of interest or the point of interest on the image as described above.

In the foregoing explanation, the X-ray system has the imaging geometrical model and the imaging parameters of the camera that are obtained by demarcating, and the height of the X-ray source from the examining table (i.e., the patient), the relationship between the size of the collimator shutter and the size of the region of the field of view for exposure and so on, stored thereon in advance. For example, the camera 208 may be demarcated before the X-ray system according to at least one embodiment the present invention is delivered, and the obtained imaging geometrical model and the imaging parameters are recorded in the X-ray system for use later by the computing device 209. In addition, parameters such as the current position of the X-ray source, the current size of the collimator shutter and the like are known to the X-ray system.

In one embodiment, when the camera is demarcated, the plane where the patient lies (i.e., the plane where the examining table is located at) is taken as the XY plane of the coordinate system, with a fixed point on the examining table being the origin, since what is taken by the camera 208 in the X-ray system is the image of the patient, such a coordinate system may facilitate computation of the position and size of the field of view for exposure. Therefore, the coordinate of the center of the field of view for exposure on the Z axis of the world coordinate system is 0. The X, Y coordinates of the target position of the X-ray source equal to the X, Y coordinates of the desired field of view for exposure, the Z coordinate of the target position of the X-ray source equals to the height h of the X-ray source from the examining table (i.e., from the patient). It should be appreciated that other planes may be taken as the XY plane, or other points may be taken as the origin.

In the case of using the above coordinate system, the relationship between the coordinates $$\begin{bmatrix} u \\ v \end{bmatrix}$$

of any point on the image and its coordinates in the world coordinate system is as follows:

$$\begin{bmatrix} X \\ Y \end{bmatrix} = A \cdot \begin{bmatrix} u \\ v \end{bmatrix} \quad \text{Equation (1)}$$

where A is the imaging parameter(s) of the camera that takes the digital image, and possibly it is not a single parameter, but a matrix of parameters, combination function of a number of parameters, and the like. With camera demarcating technologies in advance (e.g., any of various methods as described above or other demarcating technologies), the imaging parameter(s) A may be obtained. Equation (1) embodies the imaging geometrical model of the camera.

In response to the selection of the region of interest or the point of interest on the image displayed in the display, the computing device 209 first computes the position of the center of the selected region of interest on the image as the position of the center of the desired field of view for exposure on the image, or computes the position of the selected point of interest on the image as the position of the center of the desired field of view for exposure on the image. Then, the computing device 209 utilizes the stored imaging parameter(s) A to compute the position of the center of the field of view for exposure in the real world (i.e., the actual position on the patient) based on Equation (1), that is:

$$\begin{bmatrix} X_0 \\ Y_0 \end{bmatrix} = A \cdot \begin{bmatrix} u_0 \\ v_0 \end{bmatrix} \quad \text{Equation (2)}$$

where $$\begin{bmatrix} X_0 \\ Y_0 \end{bmatrix}$$

is the X and Y coordinates of position of the center of the field of view for exposure on the world coordinate system in the real world (in which X axis and Y axis are in the plane where the patient lies), $$\begin{bmatrix} u_0 \\ v_0 \end{bmatrix}$$

is the coordinates of position of the center of the desired field of view for exposure on the image, computed by the computing device 209, and A is the imaging parameter(s) obtained by demarcating of the camera 208.

As described earlier, the position of the center of the field of view for exposure is the projection position of the position of the X-ray source on the surface of the patient's body. Therefore, the coordinates on X axis and Y axis of the target position of the X-ray source may also be $X_0$, $Y_0$, respectively. In addition, since the height h of the X-ray source from the plane where the patient lies remains unchanged and is known, therefore, it is known that the coordinate of the target position of the X-ray source on Z axis is h. In this way, the target position of the X-ray source is obtained.

In one embodiment, the computing device 209 further computes the distance by which the X-ray source is moved so as to reach the target position. To this end, the computing device 209 calculates the moving distance Δx and Δy based on the coordinates respectively on X axis and Y axis of the current position and the target position of the X-ray source. And then, the control device controls a shifting device such as the positioner or the OTS to move the X-ray source by Δx and Δy on X axis and Y axis, respectively, relative to the patient.

During production, the image sensor, the computing device, the control device and the display as described above may be made into separate modules and distributed across the X-ray system. For example, the image sensor is located on the bottom surface of the collimator, the computing device and the control device are located at the OTS console or the workstation communicating with the X-ray system, and the display is a display of the OTS console, the portable console or the workstation. Alternatively, the image sensor, the computing device and the control device may also be made into a self-contained module for automatically adjusting the field of view for exposure of the X-ray system, the module may be attached to the X-ray system via an interface and communicate with the X-ray system and the device provided with the display, so as to implement at least one embodiment of the present invention.

Figure 3:
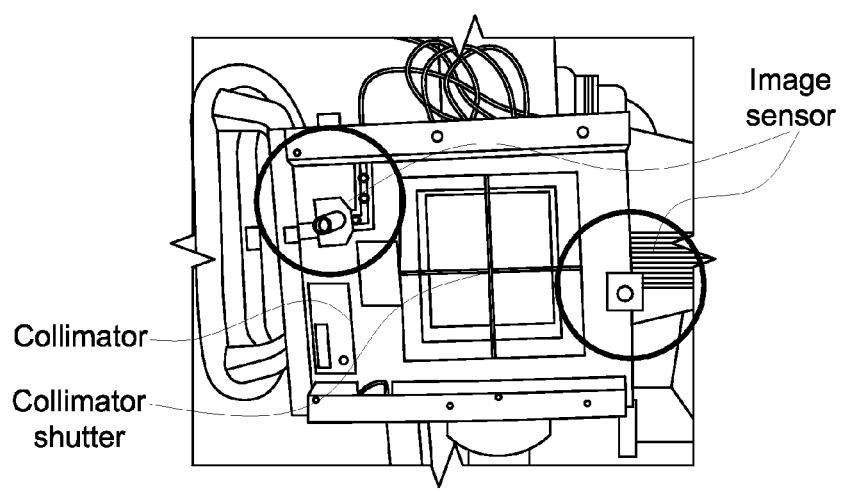
FIG. 3 is a bottom view of a collimator of an X-ray system according to an embodiment of the present invention.

Embodiments of the present invention are explained above taking a single image sensor as an example. However, it should be appreciated by those skilled in the art that multiple image sensors are applicable to embodiments of the present invention as well. By way of example, FIG. 3 is a bottom view of the collimator having two image sensors, according to an embodiment of the present invention. In the embodiment, two image sensors are arranged at different locations on the collimator. These two image sensors respectively capture images of the patient, and either of these two images is displayed on the display for selection of a region of interest or a point of interest by a user. After selection of the region of interest or the point of interest, the computing device computes the coordinates of the center of the desired field of view for exposure respectively on these two images, and computes two corresponding coordinates on the world coordinate system based on the imaging geometrical model and the imaging parameters of each of image sensors. Since distortion may occur during imaging of each camera, the computed two coordinates of the world coordinate system may not equal to each other. By combining the two coordinates of the world coordinate system to compute the final position of the center of the desired field of view for exposure, distortion error may be compensated for to some extent. For example, the final position of the center of the desired field of view for exposure may be obtained by averaging these two coordinates of the world coordinate system, or multiplying them respectively by respective weighting coefficient generated through experiments.

Figure 5:
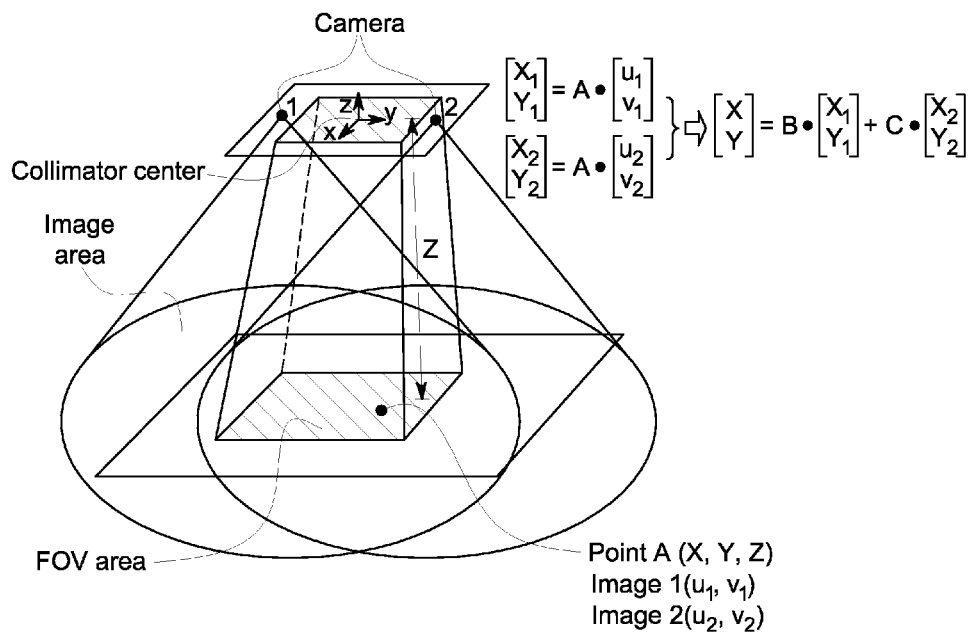
FIG. 5 is a schematic diagram illustrating computation of position and size of the field of view for exposure based on the captured image of the patient, according to an embodiment of the present invention.

FIG. 5 is a schematic diagram illustrating the computation of the position and size of the field of view for exposure in the case of two image sensors, according to an embodiment of the present invention. In the embodiment, the explanation is given taking the coordinate system described above as an example. The camera 1 and the camera 2 are arranged on the bottom surface of the collimator symmetrically about the center of the collimator, and are several centimeters away from the center of the collimator. Both the camera 1 and the camera 2 are demarcated, their imaging parameters are A1 and A2 respectively, then the relationships between the coordinates of the points in the real world and of the points in the images taken respectively by the camera 1 and the camera 2 are known as follows:

$$\begin{bmatrix} X \\ Y \end{bmatrix} = A1 \begin{bmatrix} u \\ v \end{bmatrix} \qquad \text{Equation (3)}$$

$$\begin{bmatrix} X \\ Y \end{bmatrix} = A2 \begin{bmatrix} u \\ v \end{bmatrix} \qquad \text{Equation (4)}$$

It is assumed that the selected region of interest or point of interest is point E on the image, the computing device determines the coordinates of point E on the image taken by the camera 1 as $(u_1, v_1)$, and on the image taken by the camera 2 as $(u_2, v_2)$. Then two pairs of coordinates of point E in the real world may be obtained as:

$$\begin{bmatrix} X_1 \\ Y_1 \end{bmatrix} = A1 \begin{bmatrix} u_1 \\ v_1 \end{bmatrix}$$

$$\begin{bmatrix} X_2 \\ Y_2 \end{bmatrix} = A2 \begin{bmatrix} u_2 \\ v_2 \end{bmatrix}$$

When the dual-camera system is demarcated, in addition to determining respective imaging geometrical models and imaging parameters of each of these two cameras, the weighting coefficients of the coordinates of a point in the real world that are computed based on respective imaging Equation (3) and (4) of respective cameras are also determined. That is, it is determined, by iterative experiments, what values the coefficients B and C in the following equation take will make the resultant coordinates $$\begin{bmatrix} X \\ Y \end{bmatrix}$$

closest to the actual value:

$$\begin{bmatrix} X \\ Y \end{bmatrix} = B \begin{bmatrix} X_1 \\ Y_1 \end{bmatrix} + C \begin{bmatrix} X_2 \\ Y_2 \end{bmatrix} \qquad \text{Equation (5)}$$

The coefficients B and C are also referred to as correction coefficients, once these coefficients are determined during demarcating, they, similar to parameter(s) A, are also recorded and may be applied to any subsequent X-ray examination.

Replacing the computed two pairs of coordinates $(X_1, Y_1)$ and $(X_2, Y_2)$ of point E into the above equation (5), the final coordinates of the center of the desired field of view for exposure may be obtained. As described earlier, the X and Y coordinates of the center of the desired field of view for exposure are the X and Y coordinates of the target position of the X-ray source.

Similarly, the range of the corrected desired field of view for exposure may also be computed.

With the above-mentioned embodiment with dual image sensors, distortion error may be reduced or compensated for, and the accuracy with which the field of view for exposure is adjusted may be improved.

In various embodiments described above, the image sensor may not only take a single digital image, but also take a plurality of digital images or video images, and display them on the display. The user may select a proper digital image or select a frame of image in the video as the image from which the region of interest or the point of interest is selected.

Figure 6:
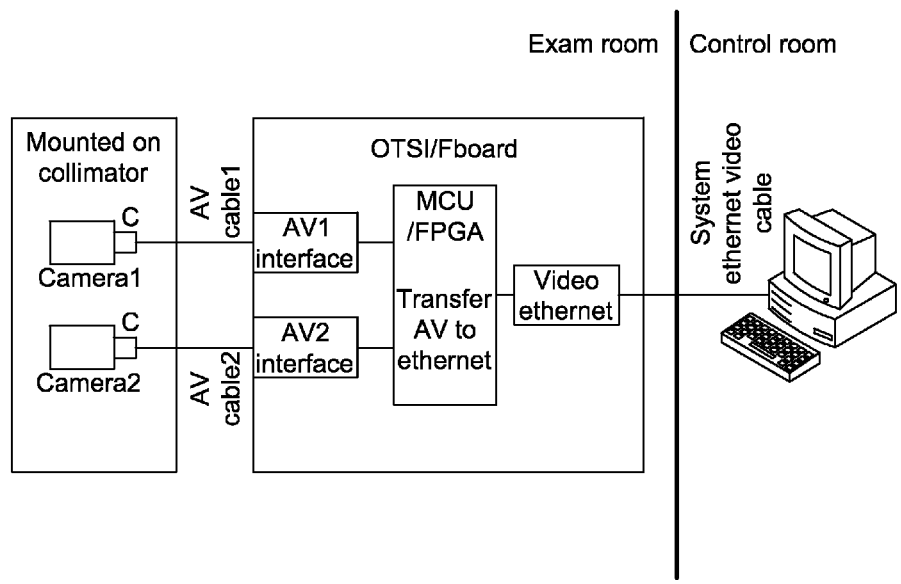
FIG. 6 is a schematic diagram of a communication line of the X-ray system according to an embodiment of the present invention.

FIG. 6 is a schematic diagram of a communication line of the X-ray system according to an embodiment of the present invention. In the embodiment, two image sensors 1 and 2 transmit the taken image or video to the OTS console, from which it is in turn transmitted to the display of the portable console or workstation. Two image sensors 1 and 2 mounted on the collimator may be connected to the AV1 interface and the AV2 interface of the OTS console respectively via the AV cable 1 and the AV cable 2. The OTS console converts the AV data from the image sensors to the Ethernet data, and transmits it to the portable console or workstation via the Ethernet video cable.

Figure 7:
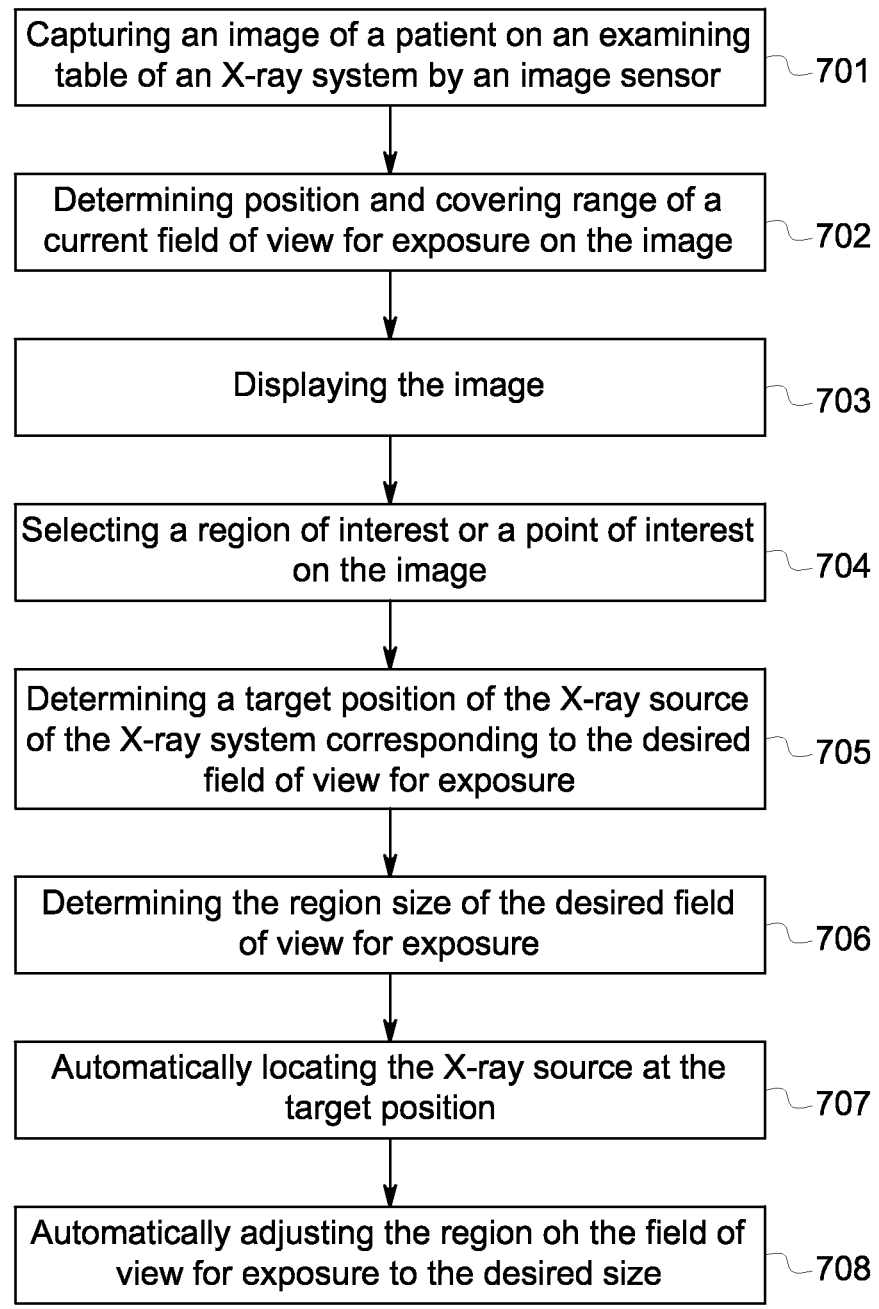
FIG. 7 is a schematic flowchart illustrating a method of automatically adjusting the field of view for exposure according to an embodiment of the present invention.

FIG. 7 is a schematic flowchart illustrating a method of automatically adjusting the field of view for exposure according to an embodiment of the present invention. In Step 701, an image of a patient on an examining table of an X-ray system is captured by an image sensor. In Step 702, the position of the center of a current field of view for exposure on the image and the covering range of the current field of view for exposure on the image are determined based on the current position of the X-ray source, the size of the collimator shutter and the imaging parameters of the image sensor. The captured image is displayed on the display (Step 703), in which the current field of view for exposure is identified on the image. The user observes whether the current field of view for exposure on the image satisfies requirements, and if so, the flow ends; if not, the user selects the region of interest or the point of interest on the image (Step 704). In response to the selection, the target position of the X-ray source of the X-ray system corresponding to the desired field of view for exposure is automatically determined (Step 705), and when the X-ray source is located at the target position, the region of interest or the point of interest falls within the desired field of view for exposure. In one embodiment, the coordinates of the position of the center of the desired field of view for exposure, within which the region of interest or the point of interest falls, on the image are first determined; and then based on the coordinates of the position and the imaging parameters of the image sensor, the coordinates of the position of the center of the desired field of view for exposure on the world coordinate system are determined; and the coordinates of the target position of the X-ray source are subsequently determined based on the known position correspondence relation between the X-ray source and the center of the field of view for exposure. Preferably, the coordinates of the center of the region of interest on the image or the coordinates of the point of interest on the image may be taken as the coordinates of the position of the center of the desired field of view for exposure on the image. In response to the selection of the region of interest or the point of interest, the region size of the desired field of view for exposure is determined based on the imaging parameters (Step 706). Step 705 and 706 may be simultaneously or sequentially performed, either Step 705 or Step 706 may be performed first. In response to the determination of the target position, the X-ray source is automatically located at the target position (Step 707). In response to the determination of the region size of the desired field of view for exposure, the region of the field of view for exposure may be adjusted to the desired size (Step 708), e.g., by adjusting the size of the collimator shutter. Similarly, Step 707 and 708 are performed in random order.

The embodiment shown in FIG. 7 is exemplary only, and not all of the steps therein are necessary. For example, any or combination of Step 702, 706, 708 may not be performed.

In one or more embodiments of the present invention, the step of automatically determining the target position of the X-ray source for the X-ray system comprises: determining the position of the center of the desired field of view for exposure on the image in response to the selection of the region of interest or the point of interest; and determining the target position of the X-ray source based on the position of the center of the desired field of view for exposure on the image and the imaging parameters of the image sensor.

In one or more embodiments of the present invention, the step of determining the target position of the X-ray source based on the position of the center of the desired field of view for exposure on the image further comprises: determining the actual position of the center of the desired field of view for exposure on the patient based on the position of the center of the desired field of view for exposure on the image and the imaging parameters of the image sensor; and determining the target position of the X-ray source based on the actual position of the center of the desired field of view for exposure on the patient and the inherent positional relationship between the X-ray source and the center.

In one or more embodiments of the present invention, the method for automatically adjusting the field of view for exposure of the X-ray system further comprises the steps of: automatically determining the size of the desired field of view for exposure in response to the selection of the region of interest on the image; and adjusting the size of a collimator shutter for the X-ray source in order to realize the size of the desired field of view for exposure.

In one or more embodiments of the present invention, the step of automatically determining the size of the desired field of view for exposure comprises: determining the coordinates of the actual positions of the points which constitute the boundary of the region of interest on the patient, based on coordinates of positions of the points which constitute the boundary on the captured image, and imaging parameters of the image sensor; determining the actual size of the region of interest based on the coordinates of the actual positions; and determining the size of the desired field of view for exposure based on the actual size of the region of interest.

In one or more embodiments of the present invention, the center of the desired field of view for exposure is the center of the region of interest or the point of interest.

In one or more embodiments of the present invention, the method for automatically adjusting the field of view for exposure of the X-ray system further comprises the steps of: determining the position of the center of a current field of view for exposure on the image based on the current position of the X-ray source and the imaging parameters of the image sensor; determining the size of the current field of view for exposure of the X-ray source on the image based on the current size of the collimator shutter of the X-ray source and the imaging parameter of the image sensor; and showing the size and the position of center of the current field of view for exposure on the captured image displayed on the display.

In one or more embodiments of the present invention, determining the target position of the X-ray source comprises determining the moving distance of the X-ray source required for realizing the desired field of view for exposure, based on the current position and the target position of the X-ray source.

In one or more embodiments of the present invention, the target position of the X-ray source refers to the target position of the X-ray source relative to the patient, wherein the X-ray source is moved the distance relative to the patient so as to be located at the target position, by moving the X-ray source via use of the overhead tube suspensory system and/or moving the patient via use of the positioner.

In one or more embodiments of the present invention, the image sensor comprises two image sensors arranged at respective predetermined positions, respectively, in the X-ray system.

In one or more embodiments of the present invention, the step of automatically determining the target position of the X-ray source for the X-ray system comprises: determining respectively the positions of the center of a desired field of view for exposure on the first and second images respectively captured by the two image sensors, in response to the selection of the region of interest or the point of interest; determining respectively the first target position corresponding to the first image and the second target position corresponding to the second image of the X-ray source, based on the positions of the center of the desired field of view for exposure on the first and second images and respective imaging parameters of the two image sensors; and obtaining the target position of the X-ray source by multiplying the first target position and the second target position respectively by corresponding predetermined weighting correction coefficients and summing the resultant products.

In one or more embodiments of the present invention, the display may be a display of the local console of the X-ray system, a display of the workstation communicating with the local console or a display of the portable console communicating with the local console or the workstation.

In one or more embodiments of the present invention, the display may be a display of the local console of the X-ray system, a display of the workstation communicating with the local console or a display of the portable console communicating with the local console or the workstation.

In one or more embodiments of the present invention, the computing device further comprises: a center of desired field of view for exposure computing unit for computing the position of the center of the desired field of view for exposure on the image; and a target position computing unit for determining the target position of the X-ray source based on the position of the center of the desired field of view for exposure on the image and the imaging parameters of the image sensor.

In one or more embodiments of the present invention, the X-ray system also comprises the size of desired field of view for exposure computing unit which is configured to automatically determine the size of the desired field of view for exposure in response to the selection of the region of interest on the image, wherein the control device adjusts the size of the collimator shutter of the X-ray source to realize the size of the desired field of view for exposure in response to the determination of the size of the desired field of view for exposure.

In one or more embodiments of the present invention, the target position computing unit determines the actual position of the center of the desired field of view for exposure on the patient based on the position of the center of the desired field of view for exposure on the image and the imaging parameters of the image sensor, and then determines the target position of the X-ray source based on the actual position of the center of the desired field of view for exposure on the patient and the inherent positional relationship between the X-ray source and the center.

In one or more embodiments of the present invention, the size of desired field of view for exposure computing unit determines the coordinates of the actual positions of the points which constitute the boundary of the region of interest on the patient, based on the coordinates of the positions of the points which constitute said boundary on the captured image and the imaging parameters of the image sensor; determines the actual size of the region of interest based on the coordinates of the actual position; and then determines the size of the desired field of view for exposure based on the actual size of the region of interest.

In one or more embodiments of the present invention, the computing device also comprises: a center of current field of view for exposure computing unit for determining the position of the center of current field of view for exposure on the image based on the current position of the X-ray source and the imaging parameters of the image sensor; a size of current field of view for exposure computing unit for determining the size of the current field of view for exposure of the X-ray source on the image based on the current size of the collimator shutter of the X-ray source and the imaging parameter of the image sensor, wherein the control device shows the size and the center of the current field of view for exposure in the image displayed on the display, based on the computed size of the current field of view for exposure on the image and the position of its center on the image.

In one or more embodiments of the present invention, the target position computing unit further computes the moving distance of the X-ray source required for realizing the desired field of view for exposure, based on the current position and the target position of the X-ray source.

In one or more embodiments of the present invention, the target position of the X-ray source refers to the target position of the X-ray source relative to the patient, wherein the shifting device comprises an overhead tube suspensory system for moving the X-ray source and a positioner for moving the patient, and wherein the X-ray source is moved the distance relative to the patient so as to be located at the target position via the overhead tube suspensory system and/or the positioner.

In one or more embodiments of the present invention, the image sensor comprises two image sensors respectively arranged at corresponding predetermined positions in the X-ray system, these two image sensor taking the first image and the second image of the patient.

In one or more embodiments of the present invention, the computing device further comprises: a desired field of view for exposure computing unit for computing the positions of the center of the desired field of view for exposure respectively on the first and second images; and a target position computing unit for determining respectively the first target position corresponding to the first image and the second target position corresponding to the second image, of the X-ray source, based on the positions of the center of the desired field of view for exposure on the first and second images and the imaging parameters of the image sensor; a weighting computing unit for obtaining the target position of the X-ray source by multiplying the first target position and the second target position respectively by corresponding predetermined weighting correction coefficients and summing the resultant products.

In comparison with the prior art, the embodiments of the present invention have one or more of the following advantages. Since the adjusting method, apparatus or X-ray system may automatically compute the proper target position of the X-ray source in response to the selection of the region of interest or the point of interest by the user on the captured image of the patient and automatically locate the X-ray source at the target position, the good adjustment of the position of the field of view for exposure of the X-ray may be achieved without requiring the radiographer to manually adjust the overhead tube suspensory system or positioner of the X-ray system. Furthermore, embodiments of the present invention may also realize the automatic adjustment of the size of the field of view for exposure. As no manual adjustment is needed, the burden on the radiographer is alleviated, while avoiding any false operation and operational error possibly caused by manual adjustment. In addition, it is not required to turn on the illumination light of the collimator of the X-ray source during automatic adjustments, the radiographer may obtain the position and range of FOV directly from the display in the control room or diagnosis room. Therefore, the patient will not be discomforted due to appearance of laser cross cursor of the illumination light. Furthermore, as the captured image may be transmitted to a remote display for selection of the region of interest or the point of interest by the user, remote and automatic adjustment of the field of view for exposure may be realized.

Furthermore, a number of images or video images of the patient may be taken or captured continuously by the image sensor in the X-ray system or the automatic adjusting device according to embodiments of the present invention. The user may select sharp images or grasp proper video frames for selection of the region of interest or the point of interest. This is particularly favorable for a restless patient (e.g., a crying infant).

Furthermore, embodiments of the present invention may employ double image sensors. Combining images from two image sensors compensates for any distortion error, thereby improving the adjustment accuracy of the field of view for exposure.

In addition, the image sensor according to embodiments of the present invention and post-processing modules (e.g., a computing device, a control device, and the like) are inexpensive. Therefore, embodiments of the present invention provide an apparatus, method and system for automatically adjusting the field of view for exposure that are cost efficient.

Still further, the apparatus, method and system for automatically adjusting the field of view for exposure according to embodiments of the present invention enable the workflow of the X-ray system to be simpler, faster, more effective, and ease to use.

Finally, one or more embodiments of the present invention may advantageously utilize a video aided technology to help a user automatically adjust the field of view for exposure. Accordingly, a user can perform the X-ray examination on a patient without manually adjusting the position and the region size of the field of view for exposure and without turning on the illumination light of the collimator, and may perform the adjustment remotely. Various embodiments of the present invention have one or more of the advantages described above.

While specific embodiments of the present invention are described above with reference to accompanying drawings, it will be understood by those skilled in the art that various changes, modifications and equivalents thereof may be made, without departing from the spirit and scope of the disclosure. These changes, modifications and equivalents are intended to fall within the spirit and scope as defined by the appended claims. Accordingly, said embodiments should not be interpreted in a limiting sense.

What is claimed is:

1. A method for automatically adjusting a field of view for exposure of an X-ray system, the method comprising:
   capturing an image of a patient on an examining table of the X-ray system by an image sensor, wherein the image sensor is placed at a predetermined position in the X-ray system;
   displaying the captured image on a display for selection of a region of interest or a point of interest by a user on the image;
   automatically determining a target position of an X-ray source in response to the selection of the region of interest or the point of interest on the image by at least:
      determining a position of a center of a desired field of view for exposure on the image in response to the selection of the region of interest or the point of interest; and
      determining the target position of the X-ray source based on the position of the center of the desired field of view for exposure on the image and imaging parameters of the image sensor by at least:
         determining an actual position of the center of the desired field of view for exposure on the patient based on the position of the center of the desired field of view for exposure on the image and the imaging parameters of the image sensor; and
         determining the target position of the X-ray source based on the actual position of the center of the desired field of view for exposure on the patient and inherent positional relationship between the X-ray source and the center,
   wherein the desired field of view for exposure covering the region of interest or the point of interest is obtained when the X-ray source is located at the target position; and
   automatically locating the X-ray source at the target position in response to the determination of the target position.

2. The method for automatically adjusting a field of view for exposure of an X-ray system according to claim 1, further comprising:
   automatically determining a size of the desired field of view for exposure in response to the selection of the region of interest on the image; and
   adjusting a size of a collimator shutter for the X-ray source in order to realize the size of the desired field of view for exposure.

3. The method for automatically adjusting a field of view for exposure of an X-ray system according to claim 2, wherein automatically determining the size of the desired field of view for exposure comprises:
   determining coordinates of actual positions of points which constitute a boundary of the region of interest on the patient, based on coordinates of positions of the points which constitute the boundary on the captured image, and imaging parameters of the image sensor;
   determining actual size of the region of interest based on the coordinates of the actual positions; and
   determining the size of the desired field of view for exposure based on the actual size of the region of interest.

4. The method for automatically adjusting a field of view for exposure of an X-ray system according to claim 1, wherein the center of the desired field of view for exposure is a center of the region of interest or the point of interest.

5. The method for automatically adjusting a field of view for exposure of an X-ray system according to claim 1, wherein determining the target position of the X-ray source comprises determining a moving distance of the X-ray source required for realizing the desired field of view for exposure, based on a current position and the target position of the X-ray source.

6. The method for automatically adjusting a field of view for exposure of an X-ray system according to claim 5, wherein the target position of the X-ray source refers to the target position of the X-ray source relative to the patient, wherein the X-ray source is moved the distance relative to the patient so as to be located at the target position, by moving the X-ray source via use of an overhead tube suspensory system and/or moving the patient via use of a positioner.

7. The method for automatically adjusting a field of view for exposure of an X-ray system according to claim 1, wherein the display may be a display of a local console of the X-ray system, a display of a workstation communicating with the local console or a display of a portable console communicating with the local console or the workstation.

8. A method for automatically adjusting a field of view for exposure of an X-ray system, the method comprising:
   capturing an image of a patient on an examining table of the X-ray system by an image sensor, wherein the image sensor is placed at a predetermined position in the X-ray system;
   displaying the captured image on a display for selection of a region of interest or a point of interest by a user on the image;
   automatically determining a target position of an X-ray source in response to the selection of the region of interest or the point of interest on the image, wherein a desired field of view for exposure covering the region of interest or the point of interest is obtained when the X-ray source is located at the target position;
   automatically locating the X-ray source at the target position in response to the determination of the target position;
   determining a position of a center of a current field of view for exposure on the image based on current position of the X-ray source and imaging parameters of the image sensor;
   determining a size of the current field of view for exposure of the X-ray source on the image based on a current size of a collimator shutter of the X-ray source and the imaging parameter of the image sensor; and
   showing the size and the position of the center of the current field of view for exposure on the captured image displayed on the display.

9. A method for automatically adjusting a field of view for exposure of an X-ray system, the method comprising:
   capturing an image of a patient on an examining table of the X-ray system by an image sensor, wherein the image sensor is placed at a predetermined position in the X-ray system;
   displaying the captured image on a display for selection of a region of interest or a point of interest by a user on the image;
   automatically determining a target position of an X-ray source in response to the selection of the region of interest or the point of interest on the image, wherein a desired field of view for exposure covering the region of interest or the point of interest is obtained when the X-ray source is located at the target position; and
   automatically locating the X-ray source at the target position in response to the determination of the target position,
   wherein the image sensor comprises two image sensors arranged at respective predetermined positions, respectively, in the X-ray system.

10. The method for automatically adjusting a field of view for exposure of an X-ray system according to claim 9, wherein automatically determining the target position of the X-ray source for the X-ray system comprises:
   determining respectively positions of a center of a desired field of view for exposure on first and second images respectively captured by the two image sensors, in response to the selection of the region of interest or the point of interest;
   determining respectively a first target position corresponding to the first image and a second target position corresponding to the second image of the X-ray source, based on the positions of the center of the desired field of view for exposure on the first and second images and respective imaging parameters of the two image sensors; and
   obtaining the target position of the X-ray source by multiplying the first target position and the second target position respectively by corresponding predetermined weighting correction coefficients and summing the resultant products.

11. An X-ray system comprising:
   an X-ray source for emitting an X-ray to form a field of view for exposure on a patient;
   an image sensor arranged at a predetermined position in the X-ray system for capturing an image of the patient;
   a display for displaying the captured image of the patient for selection of a region of interest or a point of interest by a user on the image;
   a computing device configured to compute a target position of the X-ray source, wherein a desired field of view for exposure covering the region of interest or the point of interest is obtained when the X-ray source is located at the target position, the computing device comprising:
      a first computing unit for computing a position of a center of the desired field of view for exposure on the image; and
      a target position computing unit for determining the target position of the X-ray source based on the position of the center of the desired field of view for exposure on the image and imaging parameters of the image sensor;
   a shifting device for locating the X-ray source at the target position; and
   a control device configured to control the computing device to start computing the target position in response to the selection of the region of interest or the point of interest, and to control the shifting device to locate the X-ray source at the target position in response to the computed target position.

12. The X-ray system according to claim 11, wherein the display may be a display of a local console of the X-ray system, a display of a workstation communicating with the local console or a display of a portable console communicating with the local console or the workstation.

13. The X-ray system according to claim 11, wherein the target position computing unit determines an actual position of the center of the desired field of view for exposure on the patient based on the position of the center of the desired field of view for exposure on the image and the imaging parameters of the image sensor, and then determines the target position of the X-ray source based on the actual position of the center of the desired field of view for exposure on the patient and an inherent positional relationship between the X-ray source and the center.

14. The X-ray system according to claim 11, wherein the target position computing unit further computes a moving distance of the X-ray source required for realizing the desired field of view for exposure based on a current position and the target position of the X-ray source.

15. The X-ray system according to claim 14, wherein the target position of the X-ray source refers to the target position of the X-ray source relative to the patient, wherein the shifting device comprises an overhead tube suspensory system for moving the X-ray source and a positioner for moving the patient, and wherein the X-ray source is moved the distance relative to the patient so as to be located at the target position via the overhead tube suspensory system and/or the positioner.

16. An X-ray system comprising:
an X-ray source for emitting an X-ray to form a field of view for exposure on a patient;
an image sensor arranged at a predetermined position in the X-ray system for capturing an image of the patient;
a display for displaying the captured image of the patient for selection of a region of interest or a point of interest by a user on the image;
a computing device configured to compute a target position of the X-ray source, wherein a desired field of view for exposure covering the region of interest or the point of interest is obtained when the X-ray source is located at the target position;
a shifting device for locating the X-ray source at the target position;
a control device configured to control the computing device to start computing the target position in response to the selection of the region of interest or the point of interest, and to control the shifting device to locate the X-ray source at the target position in response to the computed target position; and
a computing unit configured to automatically determine a size of the desired field of view for exposure in response to the selection of the region of interest on the image,
wherein the control device adjusts a size of a collimator shutter of the X-ray source to realize the size of the desired field of view for exposure in response to the determination of the size of the desired field of view for exposure.

17. The X-ray system according to claim 16, wherein the computing unit at least: (i) determines coordinates of actual positions of points which constitute a boundary of the region of interest on the patient based on coordinates of positions of the points which constitute the boundary on the captured image and the imaging parameters of the image sensor; and (ii) determines an actual size of the region of interest based on the coordinates of the actual positions; and then determines the size of the desired field of view for exposure based on the actual size of the region of interest.

18. An X-ray system comprising:
an X-ray source for emitting an X-ray to form a field of view for exposure on a patient;
an image sensor arranged at a predetermined position in the X-ray system for capturing an image of the patient;
a display for displaying the captured image of the patient for selection of a region of interest or a point of interest by a user on the image;
a computing device configured to compute a target position of the X-ray source, wherein a desired field of view for exposure covering the region of interest or the point of interest is obtained when the X-ray source is located at the target position;
a shifting device for locating the X-ray source at the target position;
a control device configured to control the computing device to start computing the target position in response to the selection of the region of interest or the point of interest, and to control the shifting device to locate the X-ray source at the target position in response to the computed target position;
a computing unit configured to determine a position of a center of current field of view for exposure on the image based on a current position of the X-ray source and imaging parameters of the image sensor; and
a second computing unit configured to determine a size of the current field of view for exposure of the X-ray source on the image based on a current size of a collimator shutter of the X-ray source and the imaging parameter of the image sensor,
wherein the control device shows the size and the center of the current field of view for exposure in the image displayed on the display based on the computed size of the current field of view for exposure on the image and the position of its center on the image.

19. An X-ray system comprising:
an X-ray source for emitting an X-ray to form a field of view for exposure on a patient;
an image sensor arranged at a predetermined position in the X-ray system for capturing an image of the patient;
a display for displaying the captured image of the patient for selection of a region of interest or a point of interest by a user on the image;
a computing device configured to compute a target position of the X-ray source, wherein a desired field of view for exposure covering the region of interest or the point of interest is obtained when the X-ray source is located at the target position;
a shifting device for locating the X-ray source at the target position; and
a control device configured to control the computing device to start computing the target position in response to the selection of the region of interest or the point of interest, and to control the shifting device to locate the X-ray source at the target position in response to the computed target position,
wherein the image sensor comprises two image sensors respectively arranged at corresponding predetermined positions in the X-ray system, the two image sensors taking a first image and a second image of the patient.

20. The X-ray system according to claim 19, wherein the computing device further comprises:
a desired field of view for exposure computing unit for computing positions of a center of the desired field of view for exposure respectively on the first and second images;
a target position computing unit for determining respectively a first target position corresponding to the first image and a second target position corresponding to the second image of the X-ray source based on the positions of the center of the desired field of view for exposure on the first and second images and imaging parameters of the image sensor; and
a weighting computing unit for obtaining the target position of the X-ray source by multiplying the first target position and the second target position respectively by corresponding predetermined weighting correction coefficients and summing the resultant products.

* * * * *